(12) United States Patent
Hsu et al.

(10) Patent No.: US 8,302,488 B2
(45) Date of Patent: *Nov. 6, 2012

(54) TESTING DEVICE FOR AN ELECTRONIC DEVICE HAVING TWO PIVOT POINTS

(75) Inventors: Nai-Ren Hsu, Taipei (TW); Pao-Hua Tai, Taipei (TW); Yen-Chih Chen, Taipei (TW); Pei-Fen Liu, Taipei (TW)

(73) Assignee: Inventec Corporation, Taipei (TW)

( * ) Notice: Subject to any disclaimer, the term of this patent is extended or adjusted under 35 U.S.C. 154(b) by 189 days.

This patent is subject to a terminal disclaimer.

(21) Appl. No.: 12/843,189

(22) Filed: Jul. 26, 2010

(65) Prior Publication Data

US 2011/0247428 A1 Oct. 13, 2011

(30) Foreign Application Priority Data

Apr. 7, 2010 (TW) ................................ 99110756 A

(51) Int. Cl.
*G01N 3/02* (2006.01)
*G01N 3/00* (2006.01)
*G06F 1/16* (2006.01)

(52) U.S. Cl. ...................... 73/856; 73/798; 361/679.27

(58) Field of Classification Search ................. 73/856, 73/808, 798; 361/679.27

See application file for complete search history.

(56) References Cited

U.S. PATENT DOCUMENTS

| | | | | |
|---|---|---|---|---|
| 6,272,006 | B1 * | 8/2001 | Lee | 361/679.27 |
| 6,359,774 | B1 * | 3/2002 | Leman | 361/679.27 |
| 6,530,784 | B1 * | 3/2003 | Yim et al. | 439/31 |
| 6,751,090 | B1 * | 6/2004 | Yang | 361/679.06 |
| 6,826,963 | B2 * | 12/2004 | Liu et al. | 73/798 |
| 6,850,407 | B2 * | 2/2005 | Tanimoto et al. | 361/679.27 |
| 6,912,122 | B2 * | 6/2005 | Chen et al. | 361/679.27 |
| 7,414,603 | B2 * | 8/2008 | Tseng | 345/87 |
| 7,545,108 | B2 * | 6/2009 | Flessas | 318/101 |
| 2004/0065155 | A1 * | 4/2004 | Liu et al. | 73/798 |
| 2011/0239776 | A1 * | 10/2011 | Hsu et al. | 73/856 |

* cited by examiner

*Primary Examiner* — Lisa Caputo
*Assistant Examiner* — Jonathan Dunlap
(74) *Attorney, Agent, or Firm* — J.C. Patents

(57) ABSTRACT

A testing device suitable for testing an electronic device is provided. The electronic device has a first body and a second body, wherein the first body is suitable for rotating relative to the second body. The testing device includes a carrying platform, a fixed frame, a clamping element, a first driving element, and a second driving element. The carrying platform carries the first body. The fixed frame is pivoted to the carrying platform. The clamping element is pivoted to the fixed frame for clamping the second body. The first driving element is disposed between the carrying platform and the fixed frame for driving the fixed frame to pivot relative to the carrying platform. The second driving element is disposed between the clamping element and the fixed frame for driving the clamping element to pivot relative to the fixed frame.

9 Claims, 4 Drawing Sheets

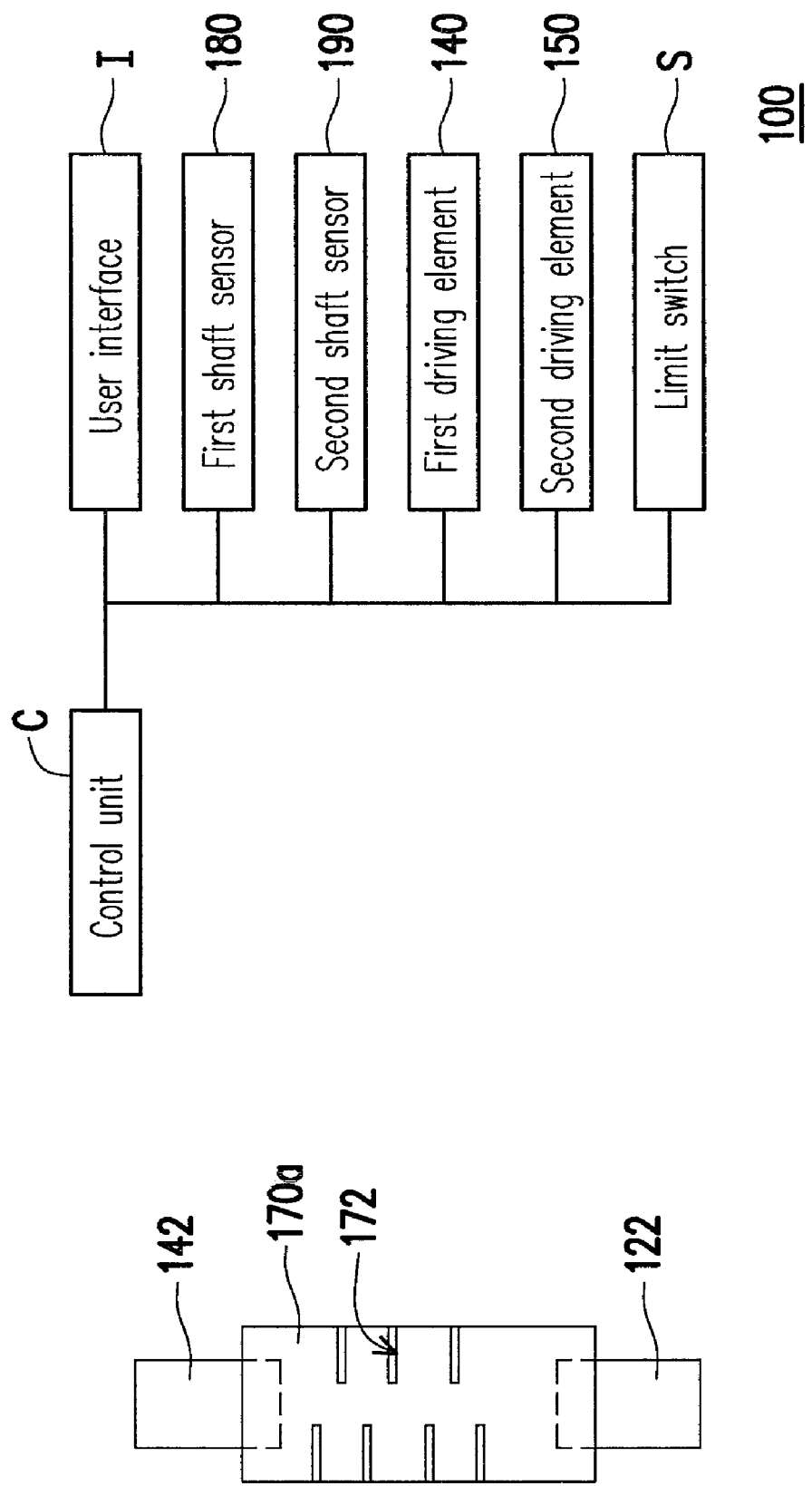

TESTING DEVICE FOR AN ELECTRONIC DEVICE HAVING TWO PIVOT POINTS

CROSS-REFERENCE TO RELATED APPLICATION

This application claims the priority benefit of Taiwan application serial no. 99110756, filed on Apr. 7, 2010. The entirety of the above-mentioned patent application is hereby incorporated by reference herein and made a part of specification.

BACKGROUND OF THE INVENTION

1. Field of the Invention

The present invention generally relates to a testing device, and more particularly, to a testing device for testing the maximum rotation number acceptable to a rotating shaft of a foldable electronic device.

2. Description of Related Art

Along with the development of electronic technology and increase in consumer demand, electronic products of lightweight, slim design, and high performance have been constantly delivered into the market. Different foldable electronic devices, such as notebook PCs, cell phones, and personal digital assistants (PDAs) have become today's mainstream products.

A foldable electronic device is usually composed of a flat panel display screen and a main body. The display screen and the main body are connected with each other by a single rotating shaft such that the display screen can pivot relative to the main body to be opened or closed. The rotating shaft of an electronic device should be able to receive the opening and closing operations for many times in order to allow the electronic device to be used for a long time. Thus, conventionally, a testing device for testing the rotating shaft of an electronic device is provided. The testing device simulates the operations of a user for opening and closing the electronic device and executes the operations repeatedly, so that whether the rotating shaft can bear enough number of the opening and closing operations or how it is broken after the limit is exceeded can be understood.

Along with the development of foldable electronic devices, the display screen of a foldable electronic device can be not only opened or closed relative to the main body but flipped so that a user can perform various functions on the display screen conveniently. However, the conventional testing device can only test the opening and closing actions in a single axial direction but not the flipping action of the display screen. Thus, the testing procedure is different from the actual use of the foldable electronic device.

SUMMARY OF THE INVENTION

Accordingly, the present invention is directed to a testing device for testing the maximum rotation number acceptable to a rotating shaft of a foldable electronic device.

The present invention provides a testing device suitable for testing an electronic device. The electronic device has a first body and a second body, wherein the first body is suitable for rotating relative to the second body. The testing device includes a carrying platform, a fixed frame, a clamping element, a first driving element, and a second driving element. The carrying platform carries the first body. The fixed frame is pivoted to the carrying platform. The clamping element is pivoted to the fixed frame for clamping the second body. The first driving element is disposed between the carrying platform and the fixed frame for driving the fixed frame to pivot relative to the carrying platform. The second driving element is disposed between the clamping element and the fixed frame for driving the clamping element to pivot relative to the fixed frame.

According to an embodiment of the present invention, the testing device further includes a first shaft sensor, a second shaft sensor, and a control unit. The first shaft sensor is disposed between the carrying platform and the fixed frame for sensing a first pivot angle of the fixed frame relative to the carrying platform. The second shaft sensor is disposed between the clamping element and the fixed frame for sensing a second pivot angle of the clamping element relative to the fixed frame. The control unit is coupled to the first driving element, the second driving element, the first shaft sensor, and the second shaft sensor. The control unit controls the first driving element and the second driving element according to the first pivot angle and the second pivot angle.

According to an embodiment of the present invention, the testing device further includes at least one limit switch. The limit switch is disposed between the carrying platform and the fixed frame or between the clamping element and the fixed frame. The limit switch is coupled to the control unit for outputting a switch signal to the control unit when the first pivot angle is greater than a first predetermined angle or the second pivot angle is greater than a second predetermined angle, so as to stop the operations of the first driving element and the second driving element.

According to an embodiment of the present invention, the clamping element includes a bracket and a plurality of clamps. The bracket is pivoted to the fixed frame. The clamps are connected to the bracket for clamping the second body.

According to an embodiment of the present invention, the bracket includes a frame body and a lifting rod. The frame body is pivoted to the fixed frame. The lifting rod is liftably disposed at the frame body, and the clamps are connected to the lifting rod.

According to an embodiment of the present invention, the clamps are respectively axially disposed to the bracket, and the clamping element further includes a plurality of elastic elements. The elastic elements are respectively disposed on the clamps for supplying an elastic force to the second body through the clamps.

According to an embodiment of the present invention, the testing device further includes a plurality of fixing elements. The fixing elements are detachably connected between the fixed frame and the clamping element for restricting the clamping element from pivoting relative to the fixed frame.

According to an embodiment of the present invention, the fixing elements are screws.

According to an embodiment of the present invention, the testing device further includes two couplings. The two couplings are respectively flexibly connected to the first driving element and the second driving element.

According to an embodiment of the present invention, the fixed frame is pivoted to the carrying platform on a first axis, and the clamping element is pivoted to the fixed frame on a second axis, wherein the first axis is perpendicular to the second axis.

As described above, the testing device provided by the present invention can test a foldable electronic device also in an axial direction between the second body and the first body besides the conventional signal axial direction.

BRIEF DESCRIPTION OF THE DRAWINGS

The accompanying drawings are included to provide a further understanding of the invention, and are incorporated

FIG. 3 is a diagram of a coupling in FIG. 1.

FIG. 4 is a circuit block diagram of the testing device in FIG. 1.

DESCRIPTION OF THE EMBODIMENTS

Figure 1:
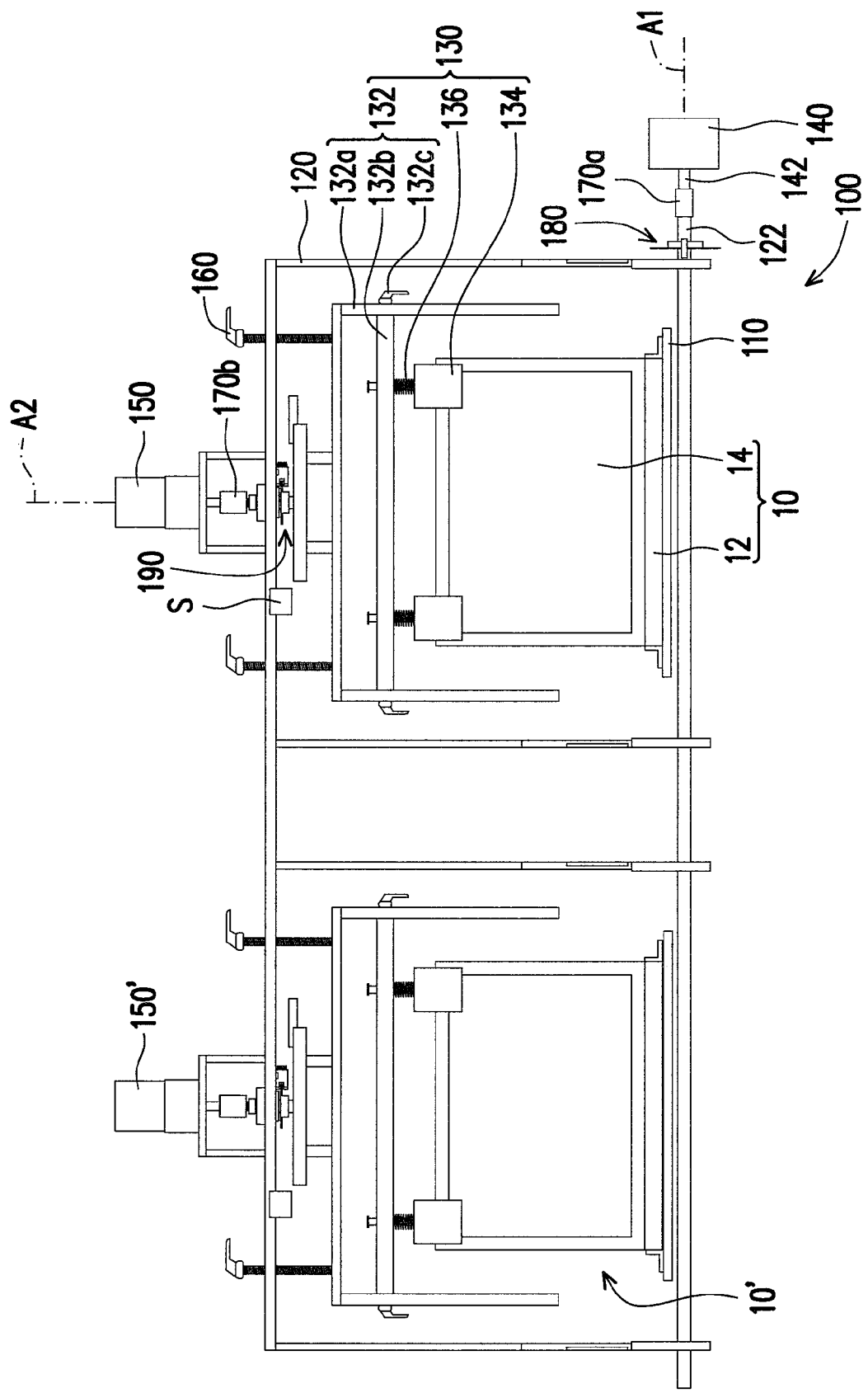
FIG. 1 is a front view illustrating how a testing device tests a foldable electronic device according to an embodiment of the present invention.

Reference will now be made in detail to the present preferred embodiments of the invention, examples of which are illustrated in the accompanying drawings. Wherever possible, the same reference numbers are used in the drawings and the description to refer to the same or like parts.

Figure 2:
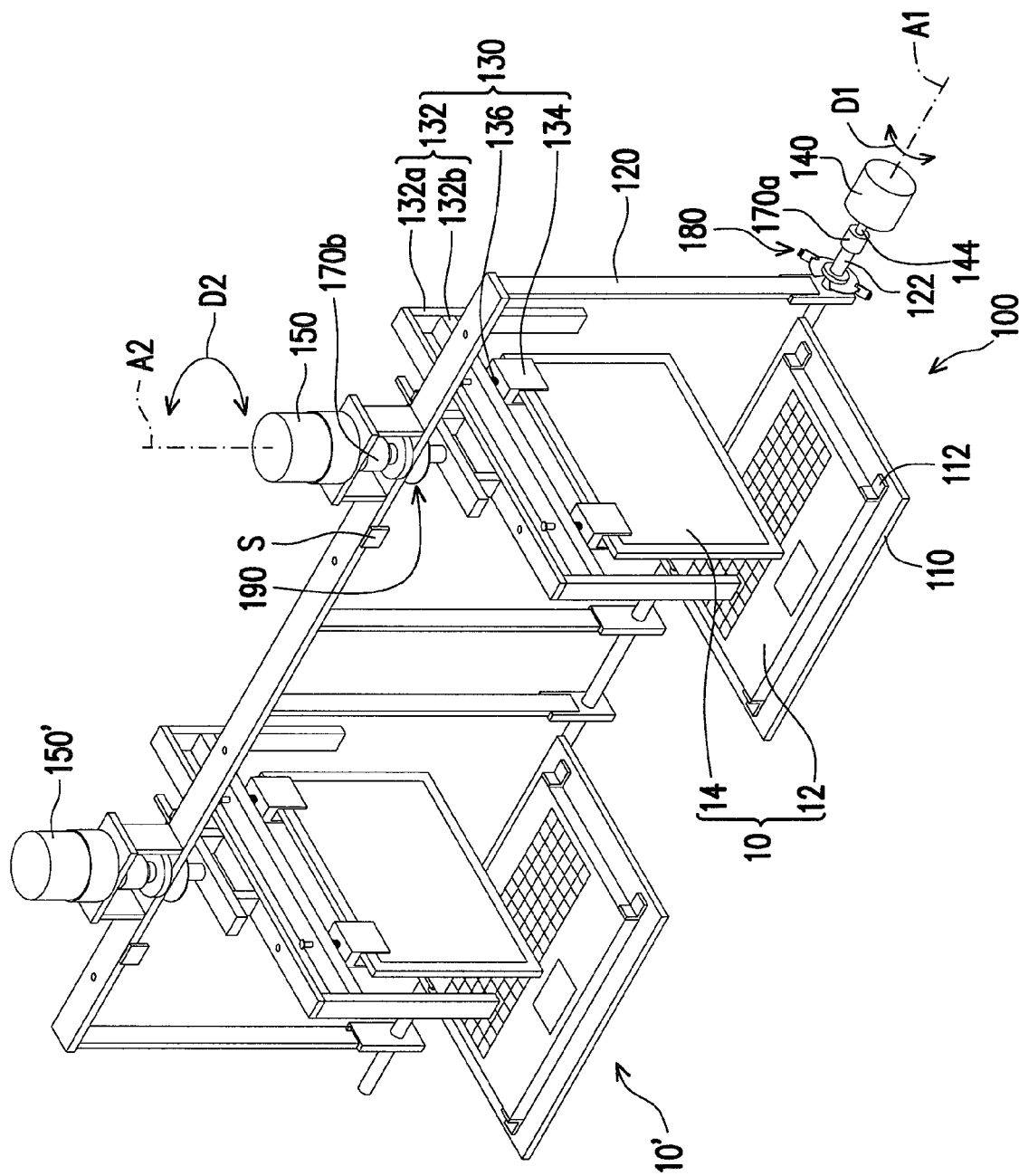
FIG. 2 is a perspective view illustrating how the testing device flips a second body of the foldable electronic device in FIG. 1.

FIG. 1 is a front view illustrating how a testing device tests a foldable electronic device according to an embodiment of the present invention. FIG. 2 is a perspective view illustrating how the testing device flips a second body of the foldable electronic device in FIG. 1. Referring to FIG. 1 and FIG. 2, the testing device 100 is suitable for performing opening, closing, and rotation tests on a foldable electronic device 10. The foldable electronic device 10 may be a notebook PC, and which includes a first body 12, a second body 14, and a rotating shaft (not shown). The first body 12 may be the main body of the notebook PC, and the second body 14 may be the display screen of the notebook PC. The rotating shaft is connected between the first body 12 and the second body 14 so that the second body 14 can be opened or flipped relative to the first body 12 on the rotating shaft.

The testing device 100 includes a carrying platform 110, a fixed frame 120, a clamping element 130, a first driving element 140, and a second driving element 150. The carrying platform 110 carries the first body 12. In the present embodiment, the carrying platform 110 has a plurality of restricting elements 112 located around the first body 12. The restricting elements 112 restrict the displacement of the first body 12 relative to the carrying platform 110.

The fixed frame 120 is pivoted to the carrying platform 110. The clamping element 130 is pivoted to the fixed frame 120 for clamping the second body 14. In the present embodiment, the fixed frame 120 is pivoted to the carrying platform 110 on a first axis A1, and the clamping element 130 is pivoted to the fixed frame 120 on a second axis A2. The first axis A1 may be perpendicular to the second axis A2.

The first driving element 140 is disposed between the carrying platform 110 and the fixed frame 120 for driving the fixed frame 120 to pivot relative to the carrying platform 110. The second driving element 150 is disposed between the clamping element 130 and the fixed frame 120 for driving the clamping element 130 to pivot relative to the fixed frame 120. In the present embodiment, the first driving element 140 and the second driving element 150 may be motors or air cylinders for respectively supplying a driving force.

When the first driving element 140 drives the fixed frame 120 to pivot in a first direction D1, the second body 14 opens or closes relative to the first body 12. When the second driving element 150 drives the clamping element 130 to pivot relative to the fixed frame 120 in a second direction D2, the second body 14 flips relative to the first body 12. Accordingly, the situation that a user uses the foldable electronic device 10 is simulated. The maximum rotation number acceptable to the rotating shaft of the foldable electronic device 10 can be tested by repeatedly performing foregoing operations.

To be specific, the clamping element 130 includes a bracket 132 and a plurality of clamps 134. The bracket 132 is pivoted to the fixed frame 120, and the clamps 134 clamp the second body 14. In the present embodiment, the bracket 132 may include a frame body 132a and a lifting rod 132b. The frame body 132a is pivoted to the fixed frame 120. The lifting rod 132b is liftably disposed at the frame body 132a so that the position thereof can be adjusted according to the size of the second body 14. Besides, the bracket 132 may further include a plurality of fastening screws 132c such that the relative position between the lifting rod 132b and the frame body 132a can be secured after the lifting rod 132b is adjusted to the appropriate position.

To be specific, the clamps 134 are respectively axially disposed to the lifting rod 132b of the bracket 132, and the clamping element 130 further includes a plurality of elastic elements 136. The elastic elements 136 are respectively disposed on the clamps 134, and the elastic elements 136 are respectively located between the lifting rod 132b and the clamps 134 and supply an elastic force to the second body 14 through the clamps 134. In the present embodiment, the elastic elements 136 may be springs having different elasticity modulus for simulating the pressing operation of a user's hand on the second body 14. Accordingly, the testing is made very close to the situation during the actual use.

Additionally, the testing device 100 further includes a plurality of fixing elements 160 detachably connected between the fixed frame 120 and the clamping element 130 for restricting the clamping element 130 from pivoting relative to the fixed frame 120. In the present embodiment, the fixing elements 160 may be screws. When the fixing elements 160 are locked to the fixed frame 120 and the clamping element 130 (as shown in FIG. 1), the second body 14 is prevented from pivoting relative to the first body 12 on the second axis A2. Namely, the testing device 100 may also be used for testing the opening and closing operations of the foldable electronic device 10 in a single axial direction, as in the conventional technique. Contrarily, when the fixing elements 160 are disassembled (as shown in FIG. 2), the testing device 100 can be used for testing the opening, closing, and flipping operations of the foldable electronic device 10 in both the directions of the first axis A1 and the second axis A2.

Additionally, the testing device 100 further includes two couplings 170a and 170b respectively flexibly connected to the first driving element 140 and the second driving element 150. FIG. 3 is a diagram of a coupling in FIG. 1. Referring to FIG. 1 and FIG. 3, taking the coupling 170a as an example, the coupling 170a is connected between an axis 142 of the first driving element 140 and an axis 122 of the fixed frame 120. The coupling 170a may have a plurality of blow holes 172 such that the coupling 170a can bend slightly to absorb the alignment tolerance between the axis 142 and the axis 122.

FIG. 4 is a circuit block diagram of the testing device in FIG. 1. Referring to FIG. 1 and FIG. 4, the testing device 100 further includes a first shaft sensor 180, a second shaft sensor 190, and a control unit C. The first shaft sensor 180 is disposed between the carrying platform 110 and the fixed frame 120 for sensing a first pivot angle of the fixed frame 120 relative to the carrying platform 110 in the first direction D1. The second shaft sensor 190 is disposed between the clamping element 130 and the fixed frame 120 for sensing a second pivot angle of the clamping element 130 relative to the fixed frame 120 in the second direction D2. The control unit C is coupled to the first driving element 140, the second driving element 150, the first shaft sensor 180, and the second shaft sensor 190. The control unit C controls the first driving element 140 and the second driving element 150 according to the first pivot angle and the second pivot angle.

Figure 5:
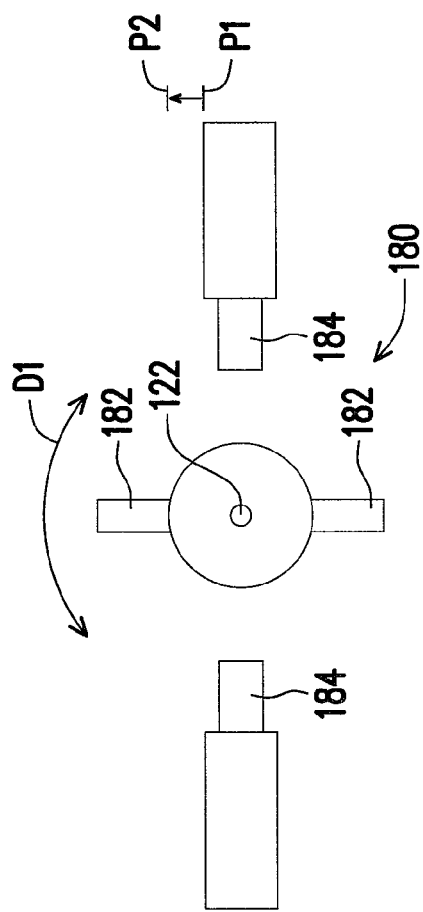
FIG. 5 is a diagram of a first shaft sensor in FIG. 1.

FIG. 5 is a diagram of a first shaft sensor in FIG. 1. Referring to FIG. 1 and FIG. 5, the first shaft sensor 180 of the testing device 100 is a magneto-inductive shaft sensor. The first shaft sensor 180 includes two magnetic elements 182, two magneto-sensitive elements 184, and a turn plate 186. The two magnetic elements 182 are connected to the turn plate 186, and the two magneto-sensitive elements 184 are respectively disposed at two sides of the turn plate 186. When the turn plate 186 rotates around the axis 122 of the fixed frame 120, it drives the two magnetic elements 182 to rotate. When the two magnetic elements 182 respectively get close to the two magneto-sensitive elements 184, the two magneto-sensitive elements 184 issue a signal to the control unit C to indicate that the first driving element 140 has pivoted a first pivot angle.

In the present embodiment, a user can determine the value of the first pivot angle by adjusting the positions of the two magneto-sensitive elements 184 relative to the turn plate 186. For example, when the two magneto-sensitive elements 184 move from a position P1 upwards to a position P2, the first pivot angle is reduced since the two magneto-sensitive elements 184 can sense the magnetic variation when the two magnetic elements 182 rotate for a smaller angle.

Figure 6:
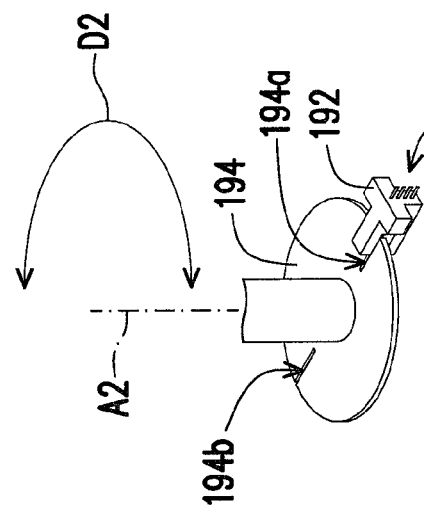
FIG. 6 is a diagram of a second shaft sensor in FIG. 1.

FIG. 6 is a diagram of a second shaft sensor in FIG. 1. Referring to FIG. 1 and FIG. 6, the second shaft sensor 190 of the testing device 100 is a notch-inductive shaft sensor. The second shaft sensor 190 includes a sensing element 192 and a turn plate 194. The turn plate 194 has a first notch 194a and a second notch 194b, wherein the first notch 194a and the second notch 194b are 180° apart. The sensing element 192 and the turn plate 194 are respectively fastened to the fixed frame 120 and the clamping element 130. When the second driving element 150 drives the clamping element 130 to rotate relative to the fixed frame 120, the clamping element 130 drives the turn plate 194 to rotate relative to the sensing element 192.

When the sensing element 192 and the first notch 194a are aligned with each other (as shown in FIG. 6), the sensing element 192 issues a detection signal to the control unit C. When the turn plate 194 continues to rotate to align the second notch 194b and the sensing element 192, the sensing element 192 issues another detection signal to the control unit C. Once the control unit C receives two consecutive detection signals, it gets to know that the clamping element 130 has pivoted the second pivot angle (for example, 180°, the angle difference between the first notch 194a and the second notch 194b) relative to the fixed frame 120. In the present embodiment, the number of notches and the angle difference between the notches can be determined according to the actual requirement.

In another embodiment that is not illustrated, the first shaft sensor 180 and the second shaft sensor 190 may be respectively implemented as a magneto-sensitive shaft sensor or a notch-inductive shaft sensor. The present invention is not limited herein.

Herein, the testing procedure will be further described in detail with reference to FIG. 1, FIG. 2, and FIG. 4. The testing device 100 further includes a user interface I. The user interface I allows a user to input test conditions, such as start time, stop time, open angle, flipping angle, and test count, etc. After the settings are done, the first shaft sensor 180 and the second shaft sensor 190 are adjusted accordingly to allow the first pivot angle and the second pivot angle to meet the test conditions (for example, 90° and 180°). After that, the user can start the test by pressing down a start button (not shown).

First, the control unit C drives the first driving element 140 to rotate in a positive direction (the clockwise direction in FIG. 2) around the first axis A1 according to the open angle (for example, greater than 90° and smaller than) 180° set by the user, so as to drive the fixed frame 120 to pivot relative to the carrying platform 110 until the second body 14 is opened relative to the first body 12 for more than a first pivot angle 90° (as illustrated in FIG. 1). Then, the first shaft sensor 180 outputs a signal to the control unit C to allow the control unit C to start the second driving element 150.

Then, the second driving element 150 drives the clamping element 130 to rotate relative to the fixed frame 120 in a reverse direction (the anticlockwise direction in FIG. 2) around the second axis A2, so as to flip the second body 14 relative to the first body 12 (as illustrated in FIG. 2) until a display area of the second body 14 is flipped to the back. When the second shaft sensor 190 detects that the clamping element 130 pivots relative to the fixed frame 120 for a second pivot angle 180°, the control unit C continues to start the first driving element 140. Then, the first driving element 140 drives the second body 14 to rotate in the reverse direction (the anticlockwise direction in FIG. 2) around the first axis A1 until the second body 14 is closed to the first body 12 so that the display area of the second body 14 faces up.

Next, the control unit C stops the first driving element 140 for a predetermined time according to the test conditions. After the predetermined time elapses, the control unit C drives the first driving element 140 to rotate in the positive direction so as to open the second body 14 relative to the first body 12. When the first shaft sensor 180 detects that the first pivot angle 90° is reached, the control unit C receives a signal from the first shaft sensor 180 and drives the second driving element 150 to rotate in the positive direction (the clockwise direction in FIG. 2).

After that, when the display area of the second body 14 turns to the front (i.e., the second shaft sensor 190 detects that the second pivot angle 180° is reached), the control unit C drives the first driving element 140 to rotate in the reverse direction around the first axis A1 so as to close the second body 14 to the first body 12. By now, the test is completed once.

Thereafter, foregoing steps are repeated for the expected number of times according to the test conditions.

In order to prevent the pivot angle from going too large and accordingly damaging the rotating shaft of the foldable electronic device 10 during the testing process, the testing device 100 may further include at least one limit switch S. The limit switch S may be disposed between the clamping element 130 and the fixed frame 120. The limit switch S is coupled to the control unit C, and which outputs a switch signal to the control unit C when the second pivot angle is greater than a second predetermined angle (for example, 180°, so as to stop the operations of the first driving element 140 and the second driving element 150.

In another embodiment that is not illustrated, the limit switch S may also be disposed between the carrying platform 110 and the fixed frame 120, and when the first pivot angle is greater than a first predetermined angle, the limit switch S outputs a switch signal to the control unit C to forcibly stop the testing process.

Additionally, in the present embodiment, the testing device 100 can test another foldable electronic device 10' at the same time while testing the foldable electronic device 10 through the extension of the fixed frame 120 and another set of components, such as a second driving element 150'. In another embodiment that is not illustrated, the testing device 100 may also test a single foldable electronic device 10 or more than two foldable electronic devices at the same time. However, the present invention is not limited herein.

In summary, the testing device in the present invention can test a foldable electronic device in two axial directions through a first driving element and a second driving element. Thereby, it satisfies today's design of the rotating shaft of the foldable electronic device.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A testing device, suitable for testing an electronic device, wherein the electronic device has a first body and a second body, and the first body is suitable for rotating relative to the second body, the testing device comprising:
   a carrying platform, for carrying the first body;
   a fixed frame, pivoted to the carrying platform;
   a clamping element, pivoted to the fixed frame, for clamping the second body;
   a first driving element, disposed between the carrying platform and the fixed frame, for driving the fixed frame to pivot relative to the carrying platform;
   a second driving element, disposed between the clamping element and the fixed frame, for driving the clamping element to pivot relative to the fixed frame;
   a first shaft sensor, disposed between the carrying platform and the fixed frame, for sensing a first pivot angle of the fixed frame relative to the carrying platform;
   a second shaft sensor, disposed between the clamping element and the fixed frame, for sensing a second pivot angle of the clamping element relative to the fixed frame; and
   a control unit, coupled to the first driving element, the second driving element, the first shaft sensor, and the second shaft sensor, for controlling the first driving element and the second driving element according to the first pivot angle and the second pivot angle.

2. The testing device according to claim 1 further comprising:
   at least one limit switch, disposed between the carrying platform and the fixed frame or between the clamping element and the fixed frame, and coupled to the control unit, for outputting a switch signal to the control unit when the first pivot angle is greater than a first predetermined angle or the second pivot angle is greater than a second predetermined angle, so as to stop operations of the first driving element and the second driving element.

3. The testing device according to claim 1, wherein the clamping element comprises:
   a bracket, pivoted to the fixed frame; and
   a plurality of clamps, connected to the bracket, for clamping the second body.

4. The testing device according to claim 3, wherein the bracket comprises:
   a frame body, pivoted to the fixed frame; and
   a lifting rod, liftably disposed at the frame body, wherein the clamps are connected to the lifting rod.

5. The testing device according to claim 3, wherein the clamps are respectively axially disposed to the bracket, and the clamping element further comprises:
   a plurality of elastic elements, disposed on the clamps, for supplying an elastic force to the second body through the clamps.

6. The testing device according to claim 1 further comprising:
   a plurality of fixing elements, detachably connected between the fixed frame and the clamping element, for restricting the clamping element from pivoting relative to the fixed frame.

7. The testing device according to claim 6, wherein the fixing elements are screws.

8. The testing device according to claim 1 further comprising:
   two couplings, respectively flexibly connected to the first driving element and the second driving element.

9. The testing device according to claim 1, wherein the fixed frame is pivoted to the carrying platform on a first axis, the clamping element is pivoted to the fixed frame on a second axis, and the first axis is perpendicular to the second axis.

* * * * *